US008226706B2

(12) United States Patent
Hartley et al.

(10) Patent No.: US 8,226,706 B2
(45) Date of Patent: Jul. 24, 2012

(54) STENT GRAFT WITH INTEGRAL SIDE ARM

(75) Inventors: David Ernest Hartley, Subiaco (AU);
Erik E. Rasmussen, Slagelse (DK);
Krasnodar Ivancev, Lund (SE)

(73) Assignees: Cook Medical Technologies LLC,
Bloomington, IN (US); **William A.
Cook Australia Pty. Ltd.**, Queensland
(AU)

( * ) Notice: Subject to any disclaimer, the term of this patent is extended or adjusted under 35 U.S.C. 154(b) by 319 days.

(21) Appl. No.: 11/663,520

(22) PCT Filed: Sep. 21, 2005

(86) PCT No.: PCT/US2005/033800
§ 371 (c)(1),
(2), (4) Date: Oct. 11, 2007

(87) PCT Pub. No.: WO2006/036690
PCT Pub. Date: Apr. 6, 2006

(65) Prior Publication Data
US 2011/0288627 A1 Nov. 24, 2011

Related U.S. Application Data

(60) Provisional application No. 60/611,931, filed on Sep. 22, 2004.

(51) Int. Cl.
*A61F 2/82* (2006.01)
(52) U.S. Cl. ............... 623/1.23; 623/1.13; 623/1.11; 623/1.12

(58) Field of Classification Search ................... None
See application file for complete search history.

(56) References Cited

U.S. PATENT DOCUMENTS

| 5,824,040 | A | * | 10/1998 | Cox et al. ............... 623/1.35 |
| 590,471 | A | | 5/1999 | Leschinsky et al. |
| 6,334,867 | B1 | * | 1/2002 | Anson ................. 623/1.13 |
| 6,458,152 | B1 | * | 10/2002 | Khosravi et al. .......... 623/1.13 |
| 6,537,284 | B1 | * | 3/2003 | Inoue ................... 606/108 |
| 6,773,453 | B2 | * | 8/2004 | Ravenscroft ............. 623/1.13 |
| 6,949,121 | B1 | * | 9/2005 | Laguna ................ 623/1.35 |
| 2004/0073288 | A1 | | 4/2004 | Kerr |
| 2005/0182476 | A1 | * | 8/2005 | Hartley et al. ........... 623/1.11 |

FOREIGN PATENT DOCUMENTS
WO WO 2004/049977 6/2004
* cited by examiner

*Primary Examiner* — Thomas J Sweet
*Assistant Examiner* — Rebecca Straszheim
(74) *Attorney, Agent, or Firm* — Richard J. Godlewski

(57) ABSTRACT

A fenestrated stent graft with a tubular side arm extending there from in which the side arm can be turned inside out to extend into the stent graft during deployment of the stent graft and extended out during deployment. Also disclosed is a deployment device for such a side arm stent graft which has a deployment catheter and a side arm guide, the side arm guide is releasably fastened at a proximal end to the branch tube and is able to be moved independently of the deployment catheter such that the branch tube can be extended from the tubular body of the stent graft while it is fastened onto the side arm guide. The side arm guide can be formed from a side arm catheter and a side arm guide wire carried in the side arm catheter.

9 Claims, 8 Drawing Sheets

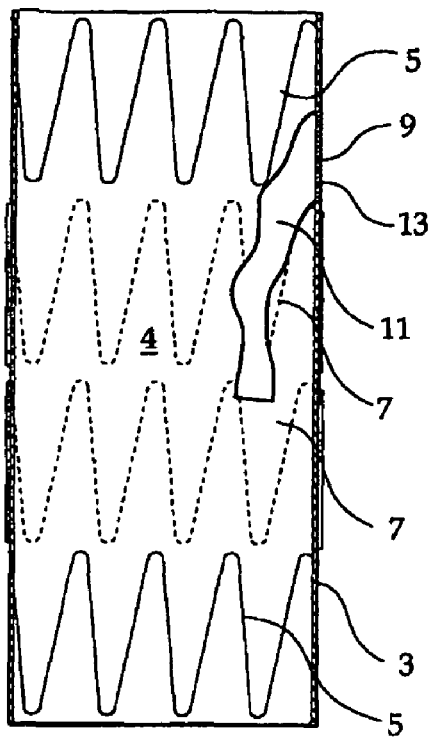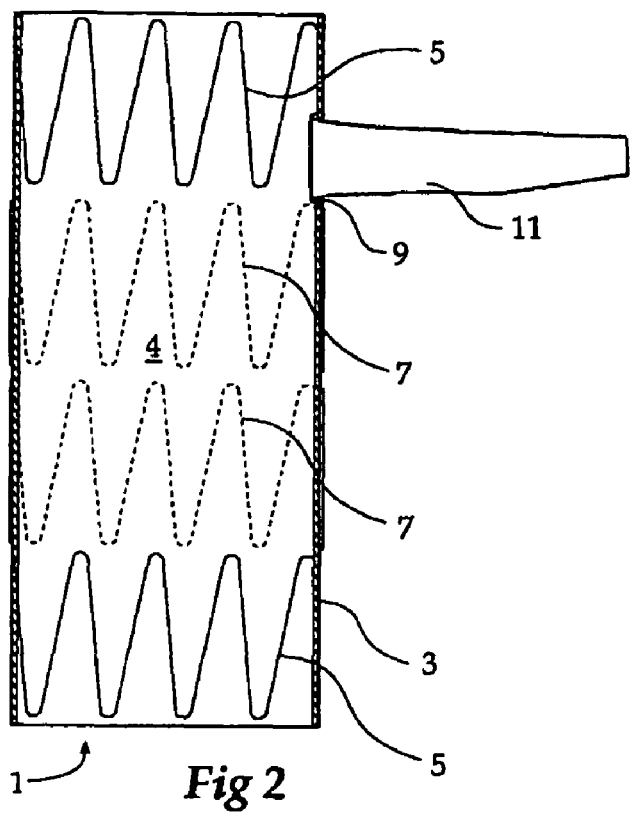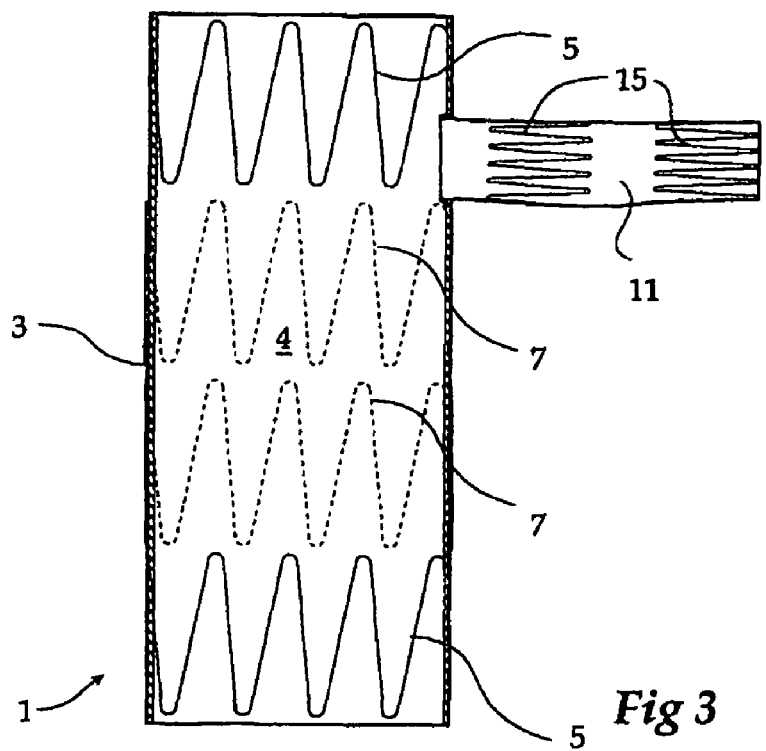

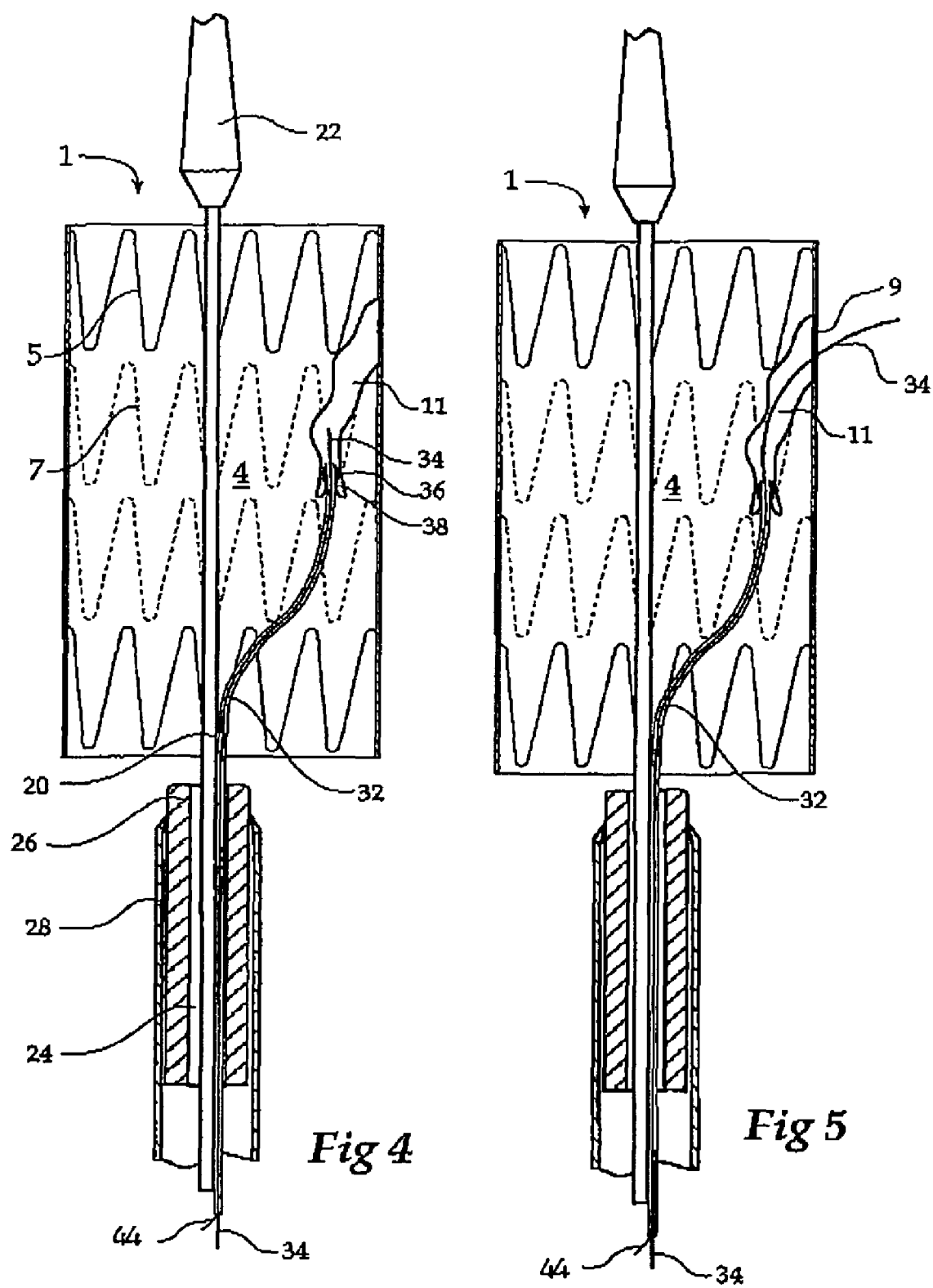

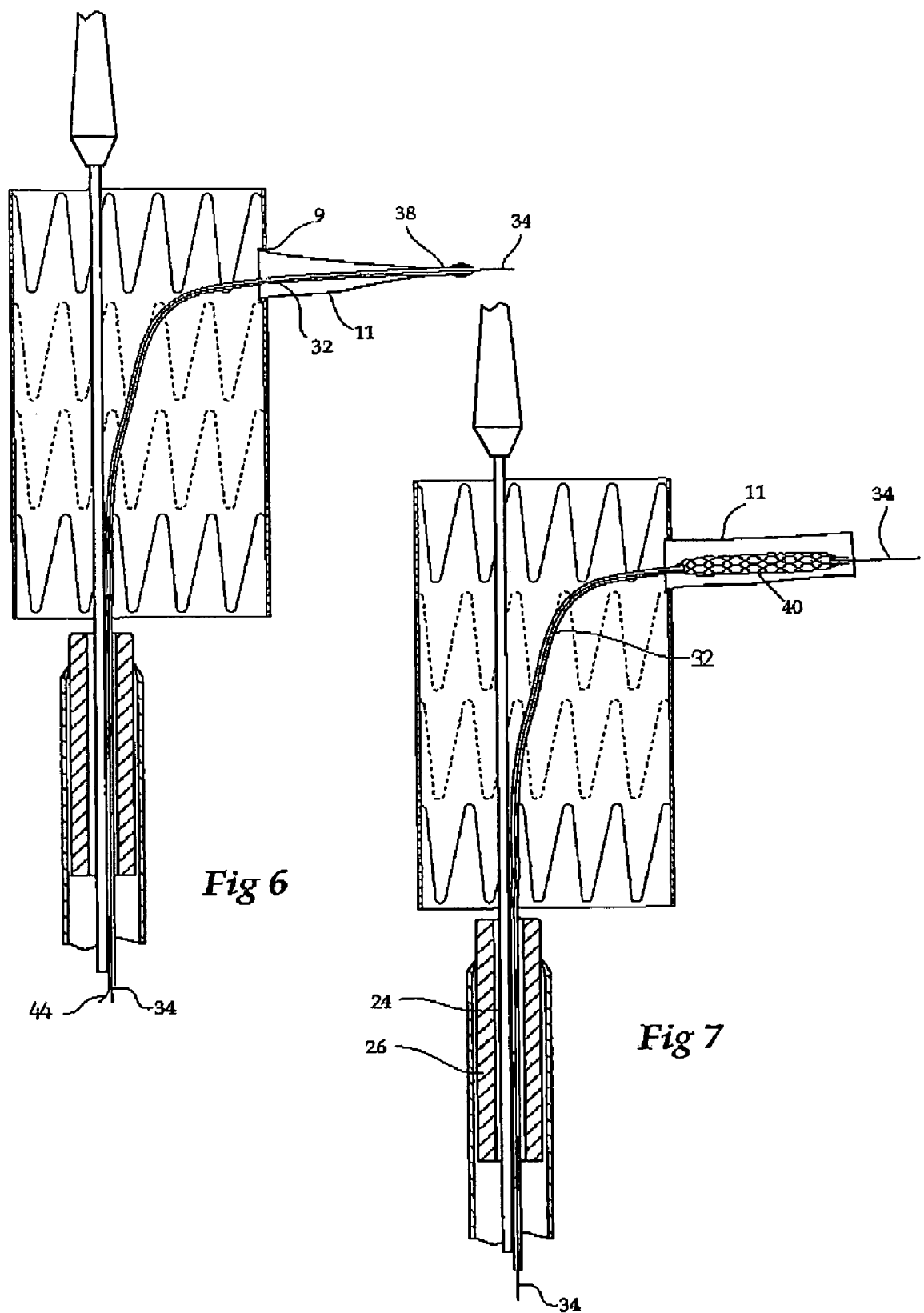

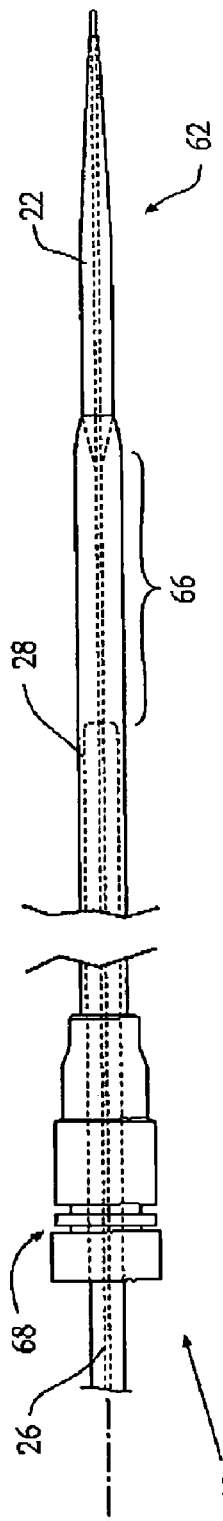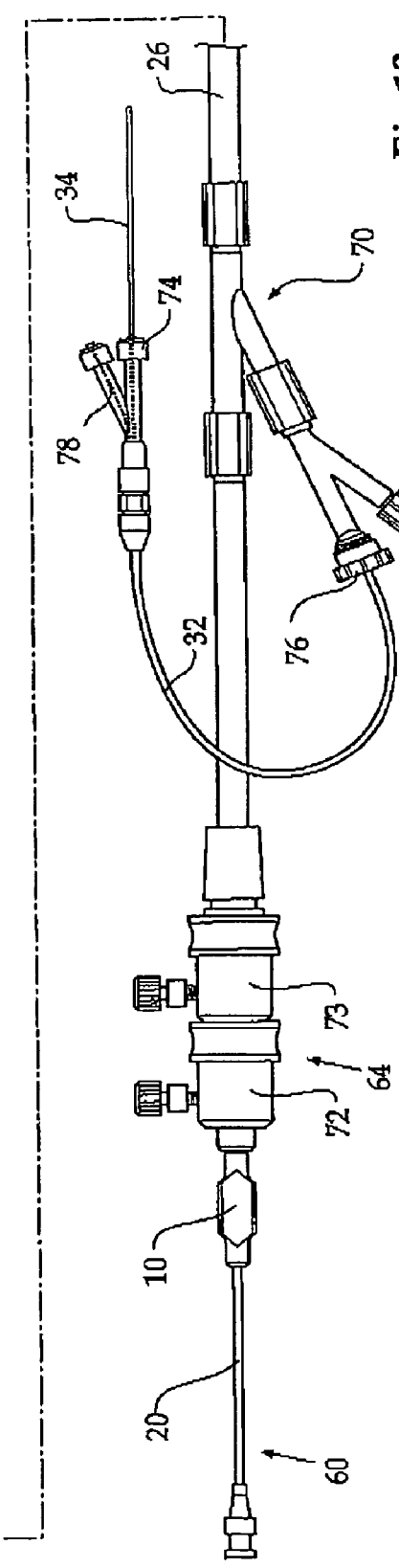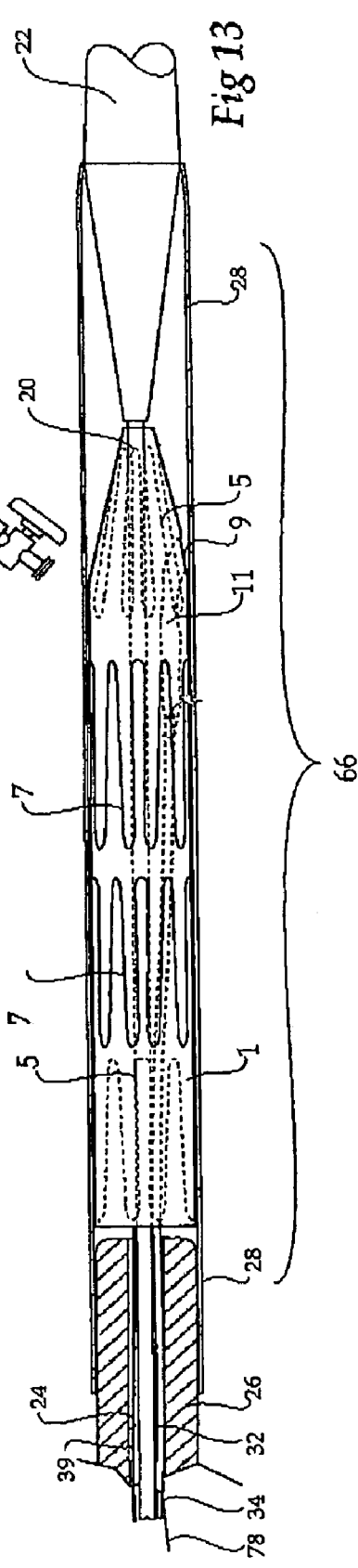
Fig 12
Fig 13

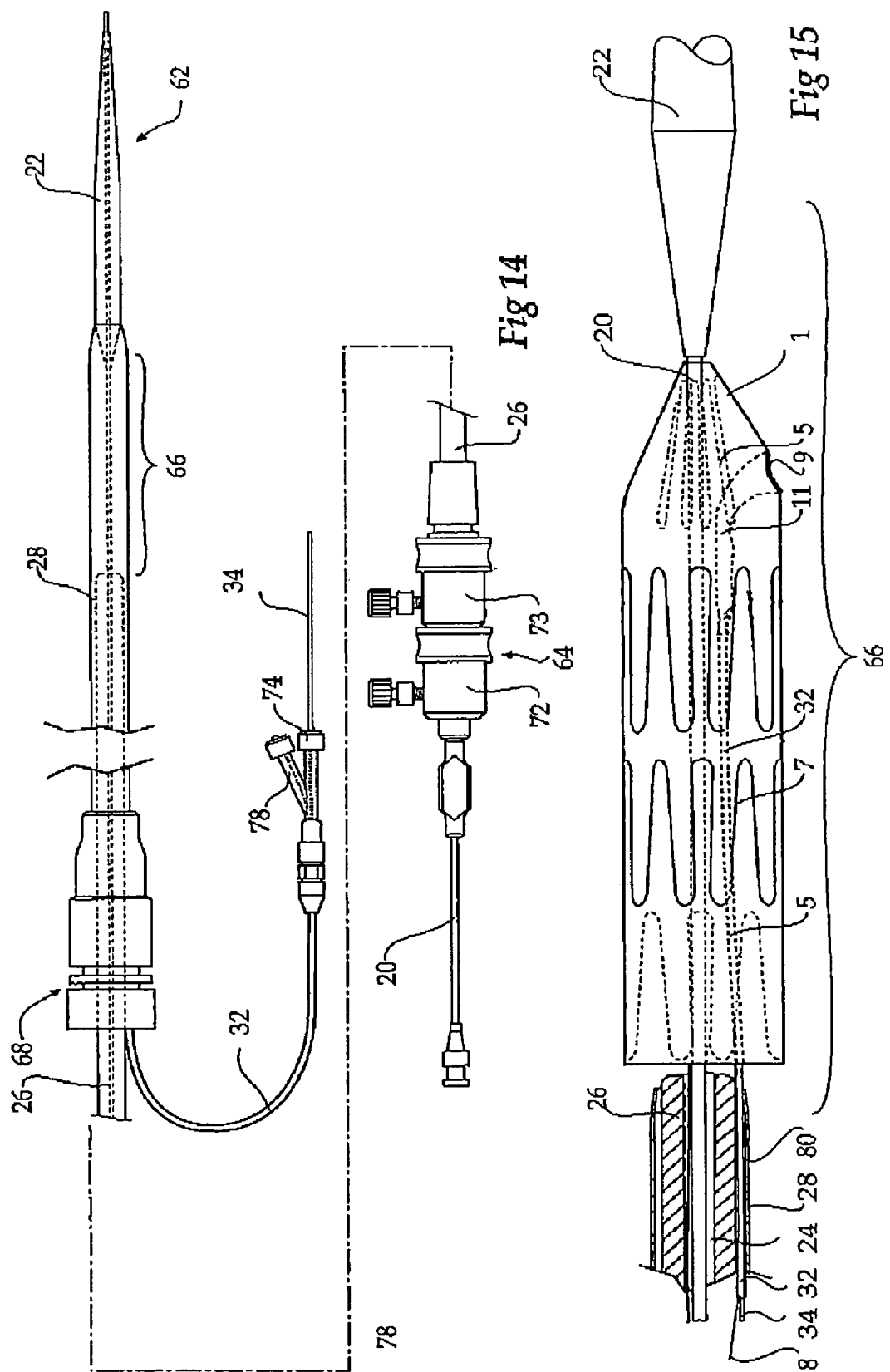

STENT GRAFT WITH INTEGRAL SIDE ARM

TECHNICAL FIELD

This invention relates to a medical device and more particularly to a medical device for deployment into a body lumen of a human or animal patient.

BACKGROUND OF THE INVENTION

Stent grafts are deployed into lumens of the human or animal body to repair or protect the wall of a vessel such as to span an aneurysm in the vessel. There are situations where the aneurysms includes a branch vessel from the lumen. In these cases spanning an aneurysm can cut-off blood flow into the branch vessel which could have serious consequences for a patient. It has been proposed to provide a fenestration in the stent graft and extend a side arm stent graft through the fenestration into the branch vessel but there can be problems with the sealing of the side arm stent graft into the main stent graft. With insufficient sealing endo leaks can occur which will continue to provide pressure into the aneurysm.

It is to this problem that the present invention is directed or at least the present invention provides a useful alternative to a physician.

Throughout this specification the term "distal", with respect to a portion of the aorta, a deployment device or a prosthesis, is the end of the aorta, deployment device or prosthesis further away in the direction of blood flow away from the heart, and the term "proximal" means the portion of the aorta, deployment device or end of the prosthesis nearer to the heart. When applied to other vessels similar terms such as "caudal" and "cranial" should be understood.

SUMMARY OF THE INVENTION

In one form therefore, although this may not necessarily be the only or broadest form, the invention is said to reside in a stent graft such as a fenestrated stent graft having a tubular body and a tubular side arm extending from the tubular body in which at least a portion of the side arm can be turned inside out to extend into the tubular body during deployment of the stent graft.

In a further form, the invention is said to reside in a stent graft having a tubular body of a biocompatible graft material and a plurality of stents to define a main lumen, at least one aperture in the tubular body defined by a peripheral edge of the aperture to define a fenestration in the tubular body, and a flexible tubular side arm sealingly fastened around the peripheral edge, the flexible tubular side arm extending into the main lumen and able to be turned inside out to extend from the tubular body, thereby providing a side arm in fluid communication with the main lumen.

By this invention there is provided a stent graft in which the side arm, at the time of delivery of the stent graft into a vessel of a patient, is within the tubular body of the stent graft but that it can be pushed out through the fenestration by turning it inside out to extend out from the fenestration into a side branch of the vessel. This arrangement ensures that the connection between the main stent graft and the side arm is a good seal because it is permanently stitched.

The graft material may be a woven or non-woven fabric such as polyester or may be a polymeric material such as expandable PTFE. The material of the flexible tubular side arm may also be a woven or non-woven fabric such as polyester or may be a polymeric material such as expandable PTFE. The graft material and that of the flexible tubular side arm may alternatively be a naturally occurring biomaterial, such as collagen, particularly a specially derived collagen material known as an extracellular matrix (ECM), such as small intestinal submucosa (SIS) able to remodel cells and tissue coming into contact therewith. Besides SIS, examples of ECM's include pericardium, stomach submucosa, liver basement membrane, urinary bladder submucosa, tissue mucosa, and dura mater. (SIS is commercially available from COOK Biotech Incorporated, West Lafayette, Ind., USA)

The plurality of stents may be self expanding stents such as zig zag stents or may be balloon expandable stents or other forms of stent.

In a further form the invention is said to reside in a stent graft comprising a tubular body of biocompatible graft material providing a main fluid flow lumen therethrough, at least one aperture in the tubular body, a branch tube of biocompatible graft material fastened at one end thereof around the at least one aperture, the tube being unstented and having a branch lumen therein and being able to extend into the main fluid flow lumen and be turned inside out to extend out from the tubular body whereby to be in fluid flow communication with the main lumen.

In a further form the invention is said to further include a deployment device for a side arm stent graft of the type discussed above, the deployment device having a deployment catheter and a side arm guide, the side arm guide being releasably fastened at a distal end to the tubular side arm or branch tube and being able to be moved independently of the deployment catheter whereby the tubular side arm or branch tube can be extended from the tubular body of the stent graft while fastened onto the side arm guide.

The side arm guide may include a guide wire and a release wire and may be carried in a side arm catheter.

To assist with the retention of the side arm onto the side arm guide wire or the side arm catheter there can be provided a grip portion for the fastening such as an "acorn" or enlarged portion on the guide wire or catheter. The grip portion is substantially at the proximal end of the side arm catheter.

The side arm guide may extend through a lumen in the deployment catheter or extend parallel to the deployment catheter within a sheath surrounding the deployment catheter.

Once the side arm has been extended from the stent graft, a stent may be placed into the side arm. To assist this process a balloon catheter may be deployed over the side arm catheter. Alternatively the side arm catheter can be withdrawn leaving the side arm guide wire in place and the balloon catheter deployed over the side arm guide wire. The stent for the side arm may be a self expanding stent such as a Cook® Zilver® Stent (Cook Incorporated, Bloomington, Ind., USA) or a balloon expandable stent.

In a further form the invention is said to further include a deployment device for a side arm stent graft of the type discussed above, the deployment device having a deployment catheter with a lumen therethrough, a guide wire catheter and a side arm catheter extending through the lumen, a side arm stent graft having a main body and a side arm received on the deployment catheter and the side arm catheter releasably mounted to the side arm whereby by movement of the side arm catheter, the side arm can be extended from the stent graft.

Preferably the side arm catheter has a side arm lumen through it and a side arm guide wire extends through the side arm lumen. A release wire for the releasable mounting of the side arm catheter to the side arm may also extend through the side arm catheter. The releasable fastening of the side arm catheter to the side arm may include a portion of suture or similar thread which includes a loop around the release wire such that removal with the release wire releases the loop and hence the releasable fastening. The release wire can extend back to a release mechanism on a handle of the deployment device.

Once the side arm is extending from the stent graft a stent may be placed into the side arm. To assist this process a balloon catheter may be deployed over the side arm catheter or side arm guide wire.

The deployment device may further include an expandable balloon on the side arm catheter distal of the releasable mounting of the side arm to the side arm catheter. The expandable balloon can carry a balloon expandable stent thereon.

The side arm stent graft of the present invention can be useful to graft, for instance, the aorta of a patient where an aneurysm incorporates or is close to branch arteries such as the renal, mesenteric or coeliac arteries. There can be more than one side arm on the stent graft.

The side arm stent graft of the present invention may enable the bridging of an aneurysed region between the stent graft and a branch artery and the permanent fastening of the side arm to the stent graft ensures a good seal to prevent endoleaks. The side arm stent graft of the present invention may also be useful for treatment of aortic dissection where the dissection region includes branch vessels.

U.S. Pat. No. 5,387,235 entitled "Expandable Transluminal Graft Prosthesis For Repair Of Aneurysm" discloses apparatus and methods of retaining grafts onto deployment devices. These features and other features disclosed in U.S. Pat. No. 5,387,235 could be used with the present invention and the disclosure of U.S. Pat. No. 5,387,235 is herewith incorporated in its entirety into this specification.

U.S. Pat. No. 5,720,776 entitled "Barb and Expandable Transluminal Graft Prosthesis For Repair of Aneurysm" discloses improved barbs with various forms of mechanical attachment to a stent. These features and other features disclosed in U.S. Pat. No. 5,720,776 could be used with the present invention and the disclosure of U.S. Pat. No. 5,720,776 is herewith incorporated in its entirety into this specification.

U.S. Pat. No. 6,206,931 entitled "Graft Prosthesis Materials" discloses graft prosthesis materials and a method for implanting, transplanting, replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herewith incorporated in its entirety into this specification.

PCT Patent Publication No. WO 98/53761 entitled "A Prosthesis And A Method And Means Of Deploying A Prosthesis" discloses an introducer for a prosthesis which retains the prosthesis so that each end can be moved independently. These features and other features disclosed in PCT Patent Publication No. WO 98/53761 could be used with the present invention and the disclosure of PCT Patent Publication No. WO 98/53761 is herewith incorporated in its entirety into this specification.

U.S. Pat. No. 6,524,335 and PCT Patent Publication No. WO 99/29262 entitled "Endoluminal Aortic Stents" disclose a fenestrated prosthesis for placement where there are intersecting arteries. This feature and other features disclosed in U.S. Pat. No. 6,524,335 and PCT Patent Publication No. WO 99/29262 could be used with the present invention and the disclosure of U.S. Pat. No. 6,524,335 and PCT Patent Publication No. WO 99/29262 is herewith incorporated in its entirety into this specification.

U.S. patent application Ser. No. 10/280,486, filed Oct. 25, 2002 and published on May 8, 2003 as U.S. Patent Application Publication No. US-2003-0088305-A1 and PCT Patent Publication No. WO 03/034948 entitled "Prostheses For Curved Lumens" discloses prostheses with arrangements for bending the prosthesis for placement into curved lumens. This feature and other features disclosed in U.S. patent application Ser. No. 10/280,486, and U.S. Patent Application Publication No. US-2003-0088305-A1 and PCT Patent Publication No. WO 03/034948 could be used with the present invention and the disclosure of U.S. patent application Ser. No. 10/280,486, and U.S. Patent Application Publication No. US-2003-0088305-A1 and PCT Patent Publication No. WO 03/034948 is herewith incorporated in its entirety into this specification.

U.S. Provisional Patent Application Ser. No. 60/392,682, filed Jun. 28, 2002, and U.S. patent application Ser. No. 10/447,406, filed May 29, 2003, and Published on Dec. 18, 2003, as US Patent Application Publication No. US-2003-0233140-A1 entitled "Trigger Wires" disclose release wire systems for the release of stent grafts retained on introducer devices. This feature and other features disclosed in U.S. Provisional Patent Application Ser. No. 60/392,682 and U.S. patent application Ser. No. 10/447,406, filed May 29, 2003 could be used with the present invention and the disclosure of U.S. Provisional Patent Application Ser. No. 60/392,682 and U.S. patent application Ser. No. 10/447,406, filed May 29, 2003 are herewith incorporated in their entirety into this specification.

U.S. Provisional Patent Application Ser. No. 60/392,667, filed Jun. 28, 2002, and U.S. patent application Ser. No. 10/609,846, filed Jun. 30, 2003, and Published on May 20, 2004, as US Patent Application Publication No. US-2004-0098079-A1, and PCT Patent Publication No. WO 2004/028399 entitled "Thoracic Deployment Device" disclose introducer devices adapted for deployment of stent grafts particularly in the thoracic arch. This feature and other features disclosed in U.S. Provisional Patent Application Ser. No. 60/392,667, U.S. patent application Ser. No. 10/609,846, and US Patent Application Publication No. US-2004-0098079-A1, and PCT Patent Publication No. WO 2004/028399 could be used with the present invention and the disclosure of U.S. Provisional Patent Application Ser. No. 60/392,667, U.S. patent application Ser. No. 10/609,846, and US Patent Application Publication No. US-2004-0098079-A1, and PCT Patent Publication No. WO 2004/028399 is herewith incorporated in its entirety into this specification.

U.S. Provisional Patent Application Ser. No. 60/392,599, filed Jun. 28, 2002, and U.S. patent application Ser. No. 10/609,835, filed Jun. 30, 2003, and published on Jun. 3, 2004, as U.S. Patent Application Publication No. US-2004-0106978-A1, and PCT Patent Publication No. WO 2004/002370 entitled "Thoracic Aortic Aneurysm Stent Graft" disclose stent grafts that are useful in treating aortic aneurysms particularly in the thoracic arch. This feature and other features disclosed in U.S. Provisional Patent Application Ser. No. 60/392,599, U.S. patent application Ser. No. 10/609,835, and U.S. Patent Application Publication No. US-2004-0106978-A1, and PCT Patent Publication No. WO 2004/002370 could be used with the present invention, and the disclosure of U.S. Provisional Patent Application Ser. No. 60/392,599, U.S. patent application Ser. No. 10/609,835, and U.S. Patent Application Publication No. US-2004-0106978-A1, and PCT Patent Publication No. WO 2004/002370 is herewith incorporated in its entirety into this specification.

U.S. Provisional Patent Application Ser. No. 60/391,737, filed Jun. 26, 2002, U.S. patent application Ser. No. 10/602, 930, filed Jun. 24, 2003, and PCT Patent Publication Number WO 2004/002365 entitled "Stent-Graft Fastening" disclose arrangements for fastening stents onto grafts particularly for exposed stents. This feature and other features disclosed in U.S. Provisional Patent Application No. 60/391,737, U.S. patent application Ser. No. 10/602,930, and PCT Patent Publication Number WO 2004/002365 could be used with the present invention and the disclosure of U.S. Provisional Patent Application Ser. No. 60/391,73, U.S. patent application Ser. No. 10/602,930, and PCT Patent Publication Number WO 2004/002365 are herewith incorporated in its entirety into this specification.

U.S. Provisional Patent Application Ser. No. 60/405,367, filed Aug. 23, 2002, U.S. patent application Ser. No. 10/647,642, filed Aug. 25, 2003, and published on Apr. 15, 2004, as U.S. Patent Application Publication No. US-2004-0073289-A1, and PCT Patent Publication No. WO 2004/017868 entitled "Asymmetric Stent Graft Attachment" disclose retention arrangements for retaining onto and releasing prostheses from introducer devices. This feature and other features disclosed in U.S. Provisional Patent Application Ser. No. 60/405,367, filed Aug. 23, 2002, U.S. patent application Ser. No. 10/647,642, filed Aug. 25, 2003, and U.S. Patent Application Publication No. US-2004-0073289-A1, and PCT Patent Publication No. WO 2004/017868 could be used with the present invention and the disclosure of U.S. Provisional Patent Application Ser. No. 60/405,367, filed Aug. 23, 2002, U.S. patent application Ser. No. 10/647,642, filed Aug. 25, 2003, and U.S. Patent Application Publication No. US-2004-0073289-A1, and PCT Patent Publication No. WO 2004/017868 is herewith incorporated in its entirety into this specification.

U.S. patent application Ser. No. 10/322,862, filed Dec. 18, 2002 and published as Publication No. US2003-0120332, and PCT Patent Publication No. WO03/053287 entitled "Stent Graft With Improved Adhesion" disclose arrangements on stent grafts for enhancing the adhesion of such stent grafts into walls of vessels in which they are deployed. This feature and other features disclosed in U.S. patent application Ser. No. 10/322,862, filed Dec. 18, 2002 and published as Publication No. US2003-0120332, and PCT Patent Publication No. WO03/053287 could be used with the present invention and the disclosure of U.S. patent application Ser. No. 10/322,862, filed Dec. 18, 2002 and published as Publication No. US2003-0120332, and PCT Patent Publication No. WO03/053287 are herewith incorporated in its entirety into this specification.

U.S. Provisional Patent Application Ser. No. 60/405,769, filed Aug. 23, 2002, U.S. patent application Ser. No. 10/645,095, filed Aug. 23, 2003, and published on Apr. 29, 2004, as U.S. Patent Application Publication No. US-2004-0082990-A1, and PCT Patent Publication No. WO 2004/017867 entitled "Composite Prostheses" discloses prostheses or stent grafts suitable for endoluminal deployment. These prostheses and other features disclosed in U.S. Provisional Patent Application Ser. No. 60/405,769, U.S. patent application Ser. No. 10/645,095, and U.S. Patent Application Publication No. US-2004-0082990-A1, and PCT Patent Publication No. WO 2004/017867 could be used with the present invention and the disclosure of U.S. Provisional Patent Application Ser. No. 60/405,769, U.S. patent application Ser. No. 10/645,095, and U.S. Patent Application Publication No. US-2004-0082990-A1, and PCT Patent Publication No. WO 2004/017867 is herewith incorporated in its entirety into this specification.

BRIEF DESCRIPTION OF THE DRAWING

This then generally describes the invention but to assist with understanding reference will now be made to the accompanying drawings which show preferred embodiments of the invention.
In the drawings:
FIG. 1 shows a stent graft according to one embodiment of the invention with a flexible side arm extending into the stent graft;
FIG. 2 shows the stent graft in FIG. 1 with the side arm turned inside out to extend out from the stent graft;
FIG. 3 shows the stent graft of FIGS. 1 and 2 with the side arm stented;
FIG. 4 shows part of a stylised deployment device which includes a side arm stent graft and side arm catheter of another form of the present invention;
FIG. 5 shows the deployment of the device of FIG. 4 with a guide wire extended through the side arm catheter;
FIG. 6 shows the embodiment of FIG. 5 with the side arm catheter extended along the guide wire to turn the side arm graft inside out;
FIG. 7 shows the deployment of a balloon catheter and balloon expandable stent over the side arm guide wire;
FIG. 12 shows a deployment device suitable for deploying a side arm stent graft of the present invention;
FIG. 13 shows a detail of a portion of the side arm stent graft deployment device of FIG. 12;
FIG. 14 shows an alternative embodiment of side arm stent graft deployment device according to the present invention;
FIG. 15 shows detail of a portion of the side arm stent graft deployment device of FIG. 14.

DETAILED DESCRIPTION

Figure 8:
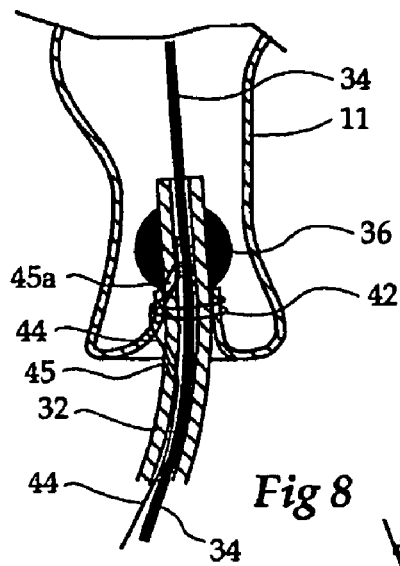
FIG. 8 shows detail of one method by which the side arm graft can be mounted on to the side arm catheter.

Now looking more closely at the drawings and first looking at an embodiment of a side arm stent graft according to the present invention as shown in FIGS. 1 to 3.

The stent graft 1 shown in cross section has a substantially tubular body 3 of a graft material defining an internal lumen 4. Self-expanding zig zag stents 5 are placed on the inside of the stent graft 1 at each end of the stent graft and between the ends further self-expanding zig zag stents 7 are placed on the outside of the stent graft. A fenestration 9 is provided in the tubular wall 3 of the stent graft 1 and a flexible tubular extension, side arm or tube 11 of a graft material extends from the fenestration into the internal lumen 4 of the stent graft 1. The tube 11 is fastened by stitching 13 around the periphery of the fenestration 9.

FIG. 2 shows that the tube 11 has been turned inside out to extend away from the stent graft through the fenestration 9. The tube 11 is unstented and at this stage is still flexible.

FIG. 3 shows two self-expanding zig zag stents 15 which have been placed into the tube 11 to make it more rigid and able to be supported in a branch vessel. For clarity, the body lumen and branch vessel are not shown in these drawings.

FIG. 4 to 7 show various stages in the deployment of a side arm stent graft. In FIGS. 4 to 7 a stylised deployment device is depicted. In FIGS. 12 to 15, two embodiments of deployment device according to the invention are shown.

FIG. 4 shows part of a deployment device which includes a guide wire catheter 20 which extends from a nose cone 22 at a proximal end of the deployment device and extends through a lumen 24 in a deployment catheter 26. The deployment catheter 26 is covered by a sleeve 28.

When the stent graft is in the process of being deployed into a body lumen, the sleeve 28 is extended forward to the nose cone 22 and holds the stent graft 1 in a compressed condition with the zig zag stents 5 and 7 in a constricted condition. As shown in FIG. 4, however, the sleeve 28 has been withdrawn to allow the stent graft 1 to expand. Releasable fastenings are generally provided at each end of the stent graft but these are not shown in this embodiment.

Examples of releasable fastenings are shown in U.S. Pat. No. 5,387,235 entitled "Expandable Transluminal Graft Prosthesis For Repair Of Aneurysm", PCT Patent Publication No. WO 98/53761 entitled "A Prosthesis And A Method And Means Of Deploying A Prosthesis" and U.S. patent application Ser. No. 10/447,406, filed May 29, 2003, and Published on Dec. 18, 2003, as US Patent Application Publication No. US-2003-0233140-A1 entitled "Trigger Wires" and the disclosure of these are herewith incorporated in their entirety into this specification.

A side arm catheter 32 also extends through the lumen 24 of the deployment catheter 26 and into the main lumen 4 of the stent graft 1. The side arm catheter 32 includes a guide wire 34 extending through the side arm catheter 32. The side arm catheter 32 also includes an "acorn" or enlargement 36 at its proximal end and the flexible tube 11 is fastened to the guide wire catheter immediately distal of the enlargement 36 as is shown in the detailed view of FIG. 8 and will be discussed in detail later.

When it is desired to deploy the side arm 11 of the stent graft the guide wire 11 is extended as shown in FIG. 5 so that it extends out through the fenestration 9 and by known radiographic techniques the guide wire can be guided into a branch vessel extending from the main vessel into which the stent graft is deployed. These techniques may include the guide wire having a preformed shape to enable it to be more easily guided into the branch vessel.

Once the guide wire 34 has been engaged into the branch vessel, the side arm catheter 32 is advanced along the guide wire 34 as shown in FIG. 6 so that the flexible side arm or tube 11 is turned inside out and extends out through the fenestration 9 and into the branch vessel.

The releasable fastening 38 can then be released as will be discussed in detail in relation to FIGS. 8 and 9 and the side arm catheter 32 removed while leaving the guide wire 34 in place.

As shown in FIG. 7, a balloon catheter with a balloon on it can then be deployed through the lumen 24 in the deployment catheter 26 and a balloon placed into the flexible side arm or tube 11. The balloon carries a balloon expandable stent in this embodiment and the balloon expandable stent 40 can be expanded to stent the side arm or tube 11 so as to retain it in the branch vessel.

FIG. 8 shows detail of one arrangement of the fastening of the flexible side arm tube or tube 11 onto the side arm catheter 32. The flexible side arm 11 is tied by means of sutures or other forms of thread 42 immediately distal of the bulge or enlargement 36 on the side arm catheter 32. A release wire 44 extends through the lumen of the side arm catheter 32 alongside the guide wire 34 and passes out an aperture 45 in the side arm catheter 32 and engages with a loop in the sutures 42. To ensure that the tip of the release wire 44 does not foul with the flexible side arm 11 the release wire 44 may be passed back into the lumen of the side arm catheter 32 through a further aperture 45a. When the release wire 44 is removed, the loop of suture 42 is released so that the fastening of the side arm to the side arm catheter is released.

Figure 9:
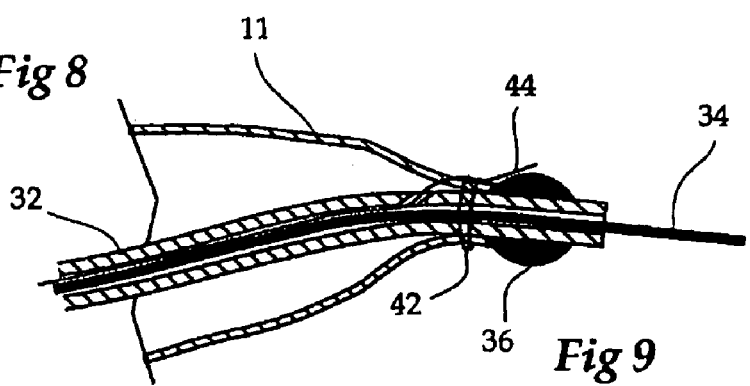
FIG. 9 shows the embodiment of FIG. 8 after the side arm graft has been turned inside out.

FIG. 9 shows a situation of the device shown in FIG. 8 when the side arm tube or tube 11 has been turned inside out. It will be noted that the sutures 42 still retain the flexible tube 11 immediately distal of the bulge or enlargement 36 onto the side arm catheter 32. Removing the release wire 44 will then release the sutures 42 so that the side arm is released.

Figure 10:
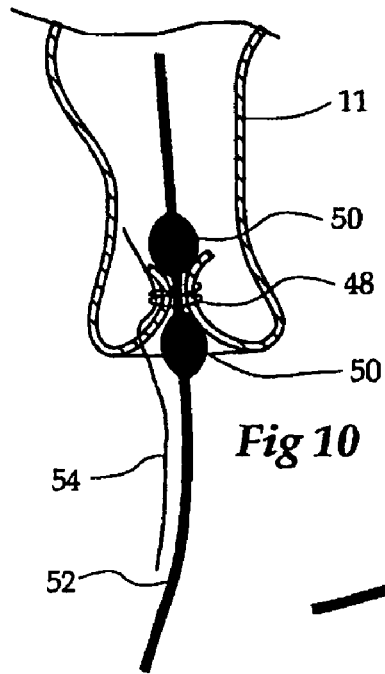
FIG. 10 shows detail of an alternative arrangement of side arm deployment using a side wire arm guide wire with the side arm graft releasably fastened to it.
Figure 11:
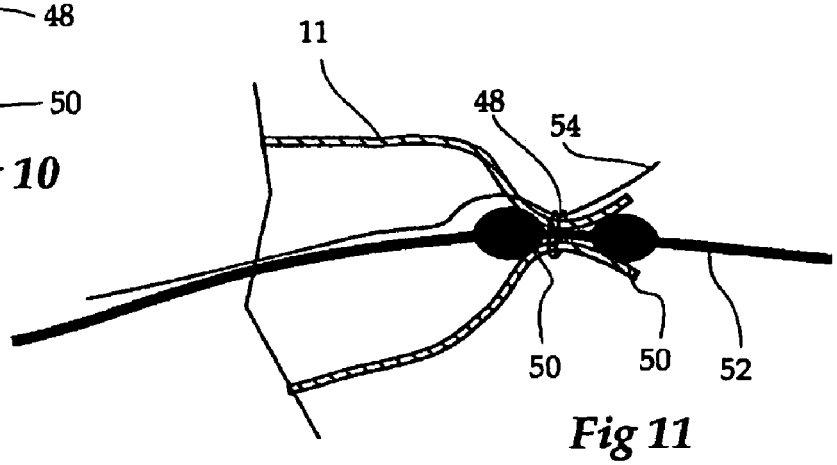
FIG. 11 shows the embodiment of FIG. 10 with the side arm graft turned inside out.

FIGS. 10 and 11 show an alternative arrangement of side arm manipulation.

In FIG. 10 the tubular side arm tube or tube 11 is fastened by means of sutures 48 between two bulges or enlargements 50 on a side arm guide wire 52. A release wire 54 extends substantially parallel to the guide wire 52 and engages the sutures 48 to enable the tubular side arm to be releasably retained to the guide wire 52. FIG. 11 shows the embodiment of FIG. 10 after the flexible side arm has been turned inside out. It will be noted that flexible side arm or tube 11 is still retained between the bulges or enlargements 50 until such time as the release wire 54 is removed to release the sutures 48.

A first embodiment of deployment device suitable to the present invention is shown in FIGS. 12 and 13. FIG. 12 shows a deployment device and FIG. 13 shows detail of one portion of the deployment device.

For ease of understanding, reference numerals used in FIGS. 12 and 13 will be the same as used in FIGS. 4 to 7 for the corresponding components.

The deployment device 19 of the present invention includes a guide wire catheter 20 which extends from a distal end 60 which is intended to remain outside a patient in use to a proximal end 62 where there is a nose cone dilator 22. A deployment catheter 26 extends from a handle portion 64 which again is intended to remain outside the patient in use to a stent graft retention region generally shown as 66. It is the stent graft retention region 66 which is shown in detail in FIG. 13. A sheath 28 extends from a sheath manipulator 68 forward to the nose cone dilator 22 to cover the stent graft during the introduction of the deployment device as can be seen in detail in FIG. 13.

A 'Y' piece 70 on the deployment catheter 26 enables the side arm catheter 32 and side arm guide wire 34 to enter the lumen 24 of the deployment catheter (see FIG. 13).

Trigger wire releases 72 and 73 on the handle 64 release fastenings at the proximal and distal ends of the stent graft 1 which is retained between the distal end of the nose cone dilator 22 and the proximal end of the deployment catheter 26 by fastenings (not shown).

To deploy the stent graft 1 within the lumen in the body, the sleeve 28 is withdrawn to allow the stent graft to expand while still being retained by the fastenings at the proximal and distal ends.

By separate manipulation of the handle and guide wire catheter, the fenestration 9 on the stent graft 1 can be aligned with a branch vessel. Locking mechanism 74 for the guide wire 34 is then released so that the guide wire can be advanced as discussed earlier, into the side vessel. Once this has been achieved, the side arm catheter lock 76 can be released slightly so that the side arm catheter 32 can be advanced into the branch vessel inverting the flexible tube 11 in doing so as discussed earlier. The side arm release wire 78 can then be withdrawn to release the side arm from the side arm catheter. The side arm catheter 32 can then be withdrawn by leaving the guide wire 34 in place so that a balloon expandable stent can then be deployed through the catheter lock 76 and the 'Y' piece 70 into the side arm as discussed in relation to FIG. 7.

FIGS. 14 and 15 show an alternative embodiment of the deployment device according to this invention.

Those components which are the same as in FIGS. 12 and 13 are given the same reference numerals.

The deployment device 19 consists of a guide wire catheter 20 which extends from a distal end 60 which is intended to remain outside a patient in use to a proximal end 62 where there is a nose cone dilator 22. A deployment catheter 26 extends from a handle portion 64 which again is intended to remain outside the patient in use to a stent graft retention region generally shown as 66. It is the stent graft retention region 66 which is shown in detail in FIG. 15. A sheath 28 extends from a sheath manipulator 68 forward to the nose cone dilator 22 to cover the stent graft during the introduction of the deployment device as can be seen in detail in FIG. 15.

In this embodiment the side arm catheter 32 does not extend through a lumen in the deployment catheter 26 but extends proximally in the toroidal space 80 between the deployment catheter 26 and the sleeve 28.

In other aspects however, the manipulation of the flexible side arm is similar to the earlier embodiments.

FIG. 15 shows the sleeve 28 withdrawn from the nose cone dilator 22 to the distal end of the deployment catheter 26 so that the stent graft 1 is expanded to more
clearly show the positioning of the side arm catheter 32.

Trigger wire releases 72 and 73 on the handle 64 release fastenings for the proximal and distal ends of the stent graft 1 retained between the distal end of the nose cone dilator 22 and the proximal end of the deployment catheter 26 by fastenings (not shown).

To deploy the stent graft 1 within the lumen in the body, the sleeve 28 is withdrawn to allow the stent graft to expand while still being retained by the fastenings at the proximal and distal ends.

By separate manipulation of the handle and guide wire catheter, the fenestration 9 on the stent graft 1 can be aligned with a branch vessel. Locking mechanism 74 for the guide wire 34 is then released so that the guide wire can be advanced as discussed earlier, into the side vessel. Once this has been achieved, the side arm catheter 32 can be advanced into the branch vessel inverting the flexible tube 11 in doing so as discussed earlier. The side arm release wire 78 can then be withdrawn to release the side arm from the side arm catheter. The side arm catheter 32 can then be withdrawn by leaving the guide wire 34 in place so that a balloon expandable stent (for instance) can then be deployed to ensure that the side arm is retained in the branch vessel.

Figure 16:
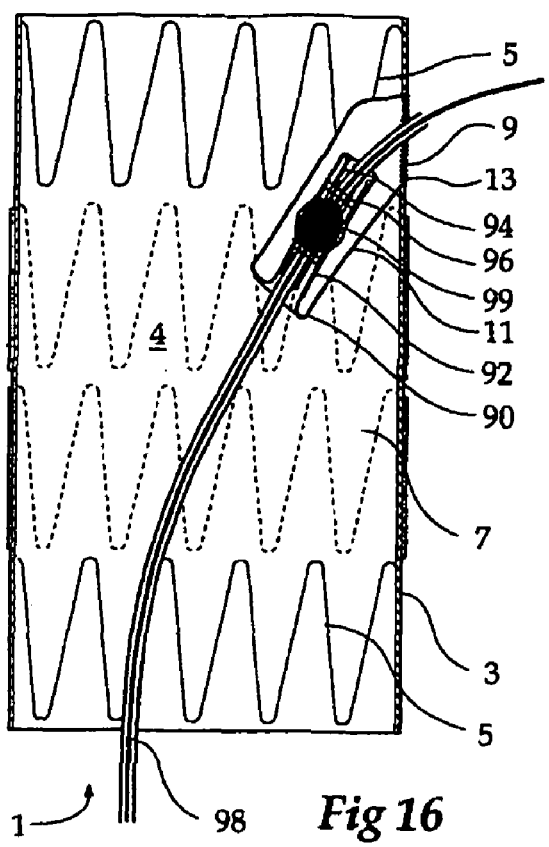
FIG. 16 shows a stent graft according to an alternative embodiment of the invention with a stented flexible side arm extending into the stent graft.
Figure 17:
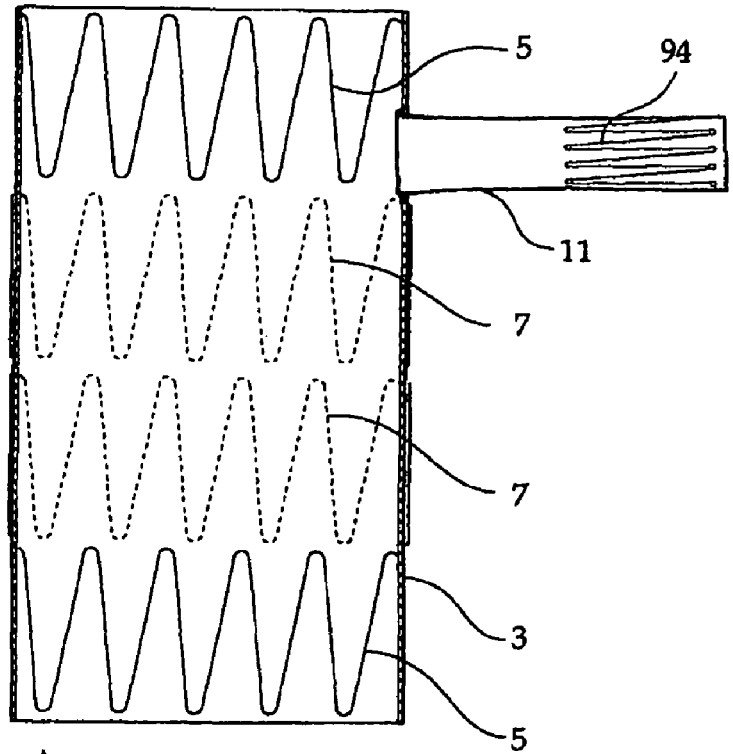
FIG. 17 shows the stent graft in FIG. 16 with the side arm extended out from the stent graft.

A further embodiment of stent graft according to the present invention is shown in FIGS. 16 and 17.

The stent graft 1 shown in cross section has a substantially tubular body 3 of a graft material defining an internal lumen 4 and in this embodiment self-expanding zig zag stents 5 are placed on the inside of the stent graft 1 at each end of the stent graft and between the ends further self-expanding zig zag stents 7 are placed on the outside of the stent graft. A fenestration 9 is provided in the tubular wall 3 of the stent graft 1 and a flexible tubular side arm or tube 11 of a graft material extends from the fenestration into the internal lumen 4 of the stent graft 1. The tube 11 is fastened by stitching 13 around the periphery of the fenestration 9 to seal to the tubular wall of the stent graft. The tube 11 is turned inside at 90 and the portion 92 extends back towards the fenestration 9. The portion 92 has at least one internal self expanding zig zag stent 94 which is held in a restrained condition by diameter reducing ties 96. The diameter reducing ties 96 also hold the tube portion 92 against a side arm catheter 98 and are preferably placed either side of a bulge or acorn 99 to prevent relative movement between the side arm catheter 98 and the tube portion 92.

As can be seen in FIG. 17 the tube 11 has been turned inside out by advancement of the side arm catheter so that the side arm 11 extends away from the stent graft through the fenestration 9. Also the diameter reducing ties 96 (see FIG. 16) have been released (by a mechanism not shown) so that the self expanding stent 94 has expanded to hold open the tube 11.

By this arrangement a stented side arm in a constrained condition can be advanced over a guide wire, in the manner discussed above, into a branch vessel of a body lumen such as an aorta and then released to allow it to expand against the wall of the branch vessel to seal therein.

Figure 18:
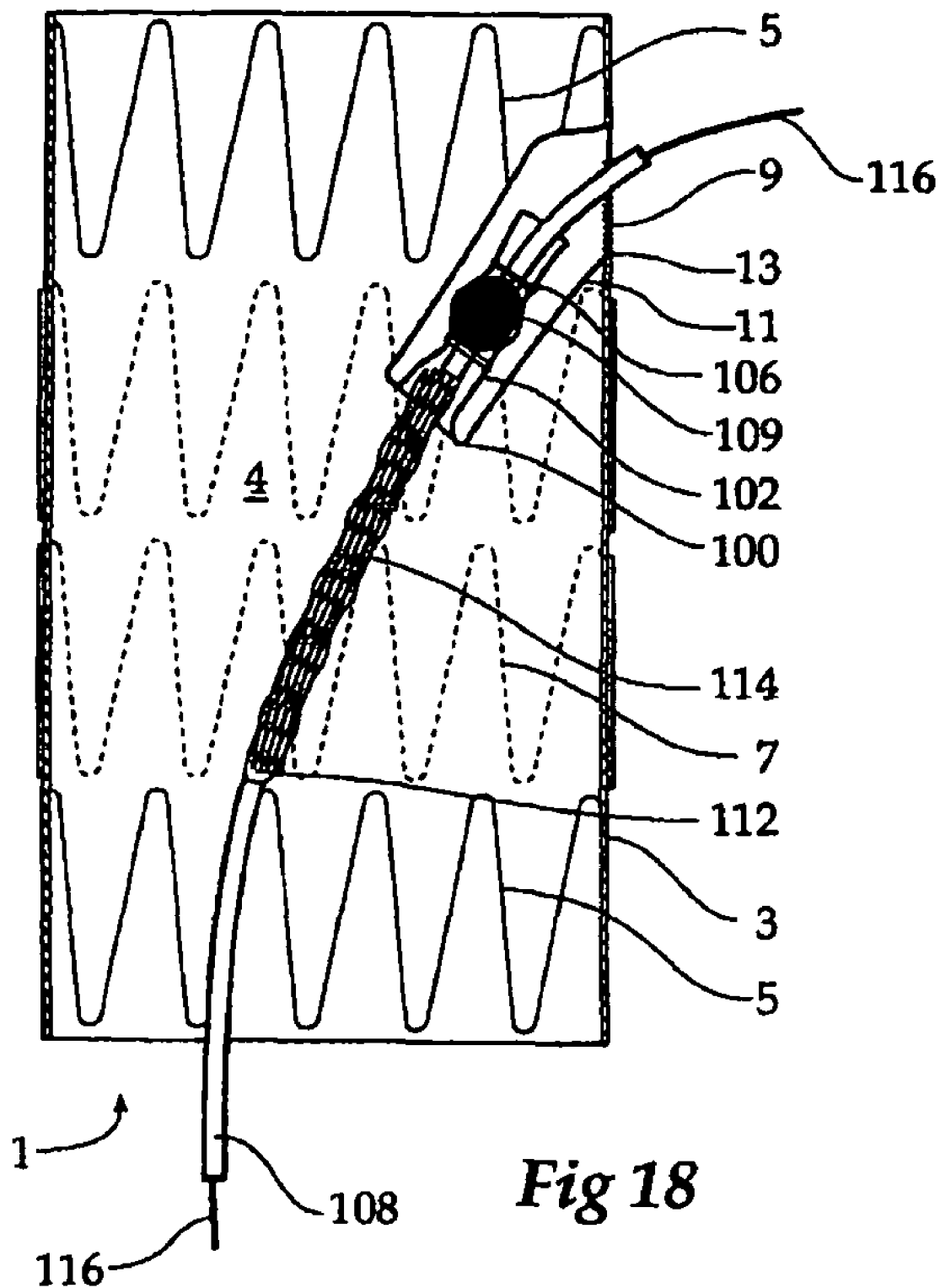
FIG. 18 shows a stent graft according to an alternative embodiment of the invention with a flexible side arm extending into the stent graft and the side arm catheter carrying a balloon expandable stent on a balloon.

FIG. 18 shows a stent graft according to an alternative embodiment of the invention with a flexible side arm extending into the stent graft and the side arm catheter carrying a balloon expandable stent on a balloon.

The stent graft generally shown as 1 has a substantially tubular body 3 of a graft material and in this embodiment, self-expanding zig zag stents 5 are placed on the inside of the stent graft 1 at each end of the stent graft and between the ends further self-expanding zig zag stents 7 are placed on the outside of the stent graft. A fenestration 9 is provided in the tubular wall 3 of the stent graft 1 and a flexible tubular side arm or tube 11 of a graft material extends from the fenestration into the internal lumen of the stent graft 1. The tube 11 is fastened by stitching 13 around the periphery of the fenestration 9 to seal to the tubular wall of the stent graft. The tube 11 is turned inside at 100 and the portion 102 extends back towards the fenestration 9. Diameter reducing ties 106 also hold the tube portion 102 against a side arm catheter 108 and are preferably placed either side of a bulge or acorn 109 to prevent relative movement between the side arm catheter 108 and the tube portion 102. The side arm catheter 108 is deployed over a side arm guide wire 116. On the side arm catheter just distal of the acorn 109 and mounted onto the side arm catheter 108 is a latex balloon 112 and mounted onto the balloon and carried by it is a balloon expandable stent 114.

In this embodiment the tube 11 is constructed from expandable PTFE and after the side arm catheter 108 has advanced over the side arm guide wire 116 into a side arm (not shown) of a blood vessel, such as a renal artery, the diameter reducing ties 106 can be removed and the side arm catheter advanced until the balloon 112 is centrally positioned within the side arm 11 and then the balloon 112 expanded. This will expand the balloon expandable stent 114 which in turn will expand the expandable PTFE side arm.

Throughout this specification various indications have been given as to the scope of the invention but the invention is not limited to any one of these but may reside in two or more of these combined together. The examples are given for illustration only and not for limitation.

The invention claimed is:
1. A combination of a stent graft and a deployment device therefor, the stent graft comprising a tubular body of a biocompatible graft material defining a main lumen there- through, at least one aperture in the tubular body, and a flexible tubular side arm sealingly fastened around the at least one aperture, the flexible tubular side arm being in an everted disposition in which it extends into the main lumen and able to be turned inside out into a non-everted disposition to extend from the tubular body, such that the flexible tubular side arm is in fluid communication with the main lumen, the deployment device comprising a deployment catheter and a guide wire catheter which extends through the deployment catheter and the main lumen, and a side arm guide, the side arm guide being releasably fastened to the flexible tubular side arm and extending through the main lumen noncoaxially and adjacent to the guidewire catheter and being capable of being moved along the main lumen independently of the guide wire catheter to push the flexible tubular side arm from its everted disposition extending into the main lumen to its non-everted disposition extending from the tubular body.

2. A combination according to claim 1, wherein the side arm guide comprises a side arm catheter and a side arm guide wire extending through the side arm catheter.

3. A combination according to claim 2, wherein flexible tubular side arm is releasably engaged with the side arm catheter.

4. A combination according to claim 1, wherein the flexible tubular side arm is unstented.

5. A combination according to claim 1, wherein the flexible tubular side arm includes at least one stent.

6. A combination according to claim 1, wherein the tubular body of a biocompatible graft material comprises a plurality of stents.

7. A combination according to claim 6, wherein the plurality of stents comprise at least one of self expanding stent and a balloon expandable stent.

8. A combination according to claim 1, wherein the flexible tubular side arm comprises a material of at least one of a woven fabric, a non-woven fabric, an expandable PTFE, a polyester and a naturally occurring biomaterial.

9. A combination according to claim 1, wherein the tubular body of a biocompatible graft material comprises at least one of a woven fabric, a non-woven fabric, an expandable PTFE, a polyester and a naturally occurring biomaterial.

* * * * *